United States Patent
Martindale et al.

(10) Patent No.: US 7,582,064 B2
(45) Date of Patent: Sep. 1, 2009

(54) SYSTEM AND METHOD FOR FOOT ASSESSMENT

(75) Inventors: Michael Martindale, 2417 NE. 32nd Ave., Portland, OR (US) 97212; Martyn Shorten, Portland, OR (US)

(73) Assignee: Michael Martindale, Portland, OR (US)

( * ) Notice: Subject to any disclaimer, the term of this patent is extended or adjusted under 35 U.S.C. 154(b) by 0 days.

(21) Appl. No.: 11/870,397

(22) Filed: Oct. 10, 2007

(65) Prior Publication Data

US 2008/0114269 A1 May 15, 2008

Related U.S. Application Data

(63) Continuation-in-part of application No. 10/808,878, filed on Mar. 24, 2004, now abandoned.

(60) Provisional application No. 60/457,869, filed on Mar. 25, 2003, provisional application No. 60/463,661, filed on Apr. 16, 2003.

(51) Int. Cl.
*A61B 5/103* (2006.01)
*A61B 5/117* (2006.01)
*A61B 5/107* (2006.01)
*G01B 1/00* (2006.01)
*A43D 1/02* (2006.01)
*A43D 1/04* (2006.01)

(52) U.S. Cl. .......... 600/592; 600/587; 33/511; 33/3 R

(58) Field of Classification Search ........... 600/592, 600/587; 33/511, 3 R
See application file for complete search history.

(56) References Cited

U.S. PATENT DOCUMENTS

| | | | |
|---|---|---|---|
| 4,662,079 | A | 5/1987 | Graf et al. |
| 4,917,105 | A | 4/1990 | Tiitola et al. |
| 4,986,534 | A | 1/1991 | Meier et al. |
| 5,206,804 | A | 4/1993 | Thies et al. |
| 6,331,893 | B1 | 12/2001 | Brown et al. |
| 2004/0193075 | A1 | 9/2004 | Martindale et al. |

*Primary Examiner*—Max Hindenburg
*Assistant Examiner*—Jeffrey G Hoekstra
(74) *Attorney, Agent, or Firm*—Ganz Law P.C.

(57) ABSTRACT

A method for assessing displacement of the talus relative to an axis of the foot and lower leg, which includes marking the anatomy of a test subject to enable tracking of the movement of the talus relative to the axis, and aligning the foot in a first position, and observing the displacement of the talus as indicated by the marking relative to the first position while allowing a displacement of the rear foot bone complex. Another embodiment includes a system for assessing pronation in a foot.

17 Claims, 20 Drawing Sheets

SYSTEM AND METHOD FOR FOOT ASSESSMENT

RELATED APPLICATIONS

This application is a Continuation-in-Part and claims priority to and the benefit of U.S. patent application Ser. No. 10/808,878, filed Mar. 24, 2004, entitled SYSTEM FOR FOOT ASSESSMENT INCLUDING A DEVICE AND METHOD, which claims priority to and the benefit of U.S. provisional patent application Nos. 60/457,869, filed Mar. 25, 2003 and 60/463,661, filed Apr. 16, 2003, the entire disclosure of which are each hereby incorporated by reference as if set forth in its entirety for all purposes.

BACKGROUND

The inventive subject matter disclosed herein generally relates to foot assessment systems to assess displacement of the talus relative to an axis of the foot and lower leg. More particularly, the inventive subject matter relates to a system and a method to assess the amount of pronation of a foot and lower extremity.

Pronation is a complex motion in three dimensions and involves rotation among multiple axes of the foot, ankle, and leg. Normally, the foot adapts to the surface it lands upon, slightly rotates inward, and flattens the arch as the heel hits the ground. The foot's ability to pronate assists the body's midstance balance and is a part of a natural shock-absorbing system.

Pronation is a tri-planar motion of the foot: it consists of eversion, abduction, and dorsiflexion at the subtalar joint. Eversion (and oppositely, inversion) occurs in the frontal plane: the foot everts when it twists outward and upward, rotating the plantar surface (or sole) away from the center. Abduction (and oppositely, adduction) occurs in the transverse plane: the foot abducts when it rotates laterally, away from center. Dorsiflexion (and oppositely, plantarflexion) occurs in the sagittal plane: the foot dorsiflexes when it moves upwards, toward the tibia.

Oppositely to pronation, supination is an outward rotation of the ankle while the outside border of the foot supports the body.

A normal amount of pronation and supination is beneficial; it is the body's way to absorb shock, create a more stable and rigid platform for push-off, and achieve dynamic balance. Excessive motion in either direction can be very problematic if not controlled and predisposes the lower extremity to injury. An excessive amount of pronation (over-pronation) can be problematic because the shifting causes increased stress on the inside, or medial aspect, of the foot, ankle, and lower leg. Over-pronation pulls on the stabilizing muscles in the lower leg (posterior tibialus). The body may compensate for over-pronation by excessive internal rotation of the lower extremity and shifting of the subtalar-joint axis and midtarsal joint axis medially, for example. This may result in injuries to the knee, ankle, lower leg, and Achilles tendon. Conversely, excessive supination stretches the stabilizing muscles on the outside of the lower leg (peroneals) and the ankle may roll over.

It is often necessary to correct foot-motion when a foot over pronates. The correction may greatly reduce the propensity for injury and improves ambulatory performance. An over-pronating foot can be corrected with remedial foot support that aligns the foot in a normal pronation-range. Orthotic-insoles, also called prescription foot orthotics, are one approach to properly align and support the foot. Orthotic insoles are custom-made inserts for shoes and are designed to correct various foot and lower body conditions. The manufacturing and materials vary based on patient needs, activities, and health factors. Another approach is to select motion-control shoes, or shoes with stabilizing features, that can correct the range of motion of an over-pronating foot.

To select the appropriate orthotic insole or motion-control shoe, the amount of pronation must be assessed. One prior-art assessment technique teaches videotaping the foot while running. Pronation is determined by viewing the motion of the rear foot, or movement of the calcaneus in the frontal plane. However, visually assessing pronation based on rear-foot motion is inaccurate. For example, a foot can exhibit a small amount of calcaneal eversion yet have severe over-pronation. Alternatively, the amount of calcaneal eversion can be limited in the frontal plane but severe rotation may occur at the metatarsal joint in the transverse plane.

Another prior art attempt to assess pronation requires a visual inspection of the worn tread on a pair of shoes. This is highly subjective, as it depends on the skill of the observer.

Another prior art assessment method quantifies the lowering of the longitudinal-arch profile. This method is unsatisfactory. For example, a foot can maintain a high arch-profile but exhibit severe transverse-plane and frontal-plane motion at the subtalar joint and midtarsal joint.

U.S. Pat. No. 4,662,079 discloses a process and apparatus for forming customized footwear by determining a range of motion from supination to pronation. The patent teaches that this is done while keeping the rear foot bone completely in a neutral position. A range-of-motion measuring apparatus is used to accurately determine the neutral position of the bone structure of the rear foot complex. However, the range of motion is determined while the foot is only semi-weight bearing, that is, when a person is sitting. The patent further discloses the use of pressure switches under a subject's foot to determine end points of motion. The prior art teaches that the neutral position of the rear foot is achieved when it is placed one third of the way from maximum pronation toward maximum supination. This has been shown to be inaccurate.

Each of these prior art methods does not efficiently or accurately assess pronation. The prior art systems are cumbersome, complicated, and require skill to use. The prior art systems are also imprecise and subjective. Therefore, there is a need for a more accurate and simpler approach of assessing pronation.

SUMMARY

The inventive subject matter offers a solution for these problems by providing a system and method for assessing displacement of the talus relative to an axis of the foot, and lower leg. Contrary to findings of the prior art, the amount of pronation (including over-pronation) is independent from arch height, rear foot to fore-foot alignment, or the position of the calcaneus relative to the lower leg. Also contrary to the teaching of the prior-art, assessing pronation does require precise measurements of the foot's movement in the three anatomical planes or measurement of the rotation of the subtalar joint and midtarsal joint.

As subsequently explained in further detail, pronation of the foot in all three planes may be directly related to corresponding movement of the talar-head. By observing the displacement of the talar-head as the foot rotates from a first, neutral position to a second, relaxed position, an amount of natural pronation may be assessed. The system and method are easy to use, do not require specialized skill, and greatly reduce subjectivity in assessing pronation.

The inventive subject matter provides for a method for assessing displacement of the talus relative to an axis of the foot and lower leg, including marking the anatomy of a test subject to enable tracking of the movement of the talus relative to the axis; aligning the foot in a first position; and observing the displacement of the talus as indicated by the marking relative to the first position while allowing a displacement of the rear foot bone complex. In the foregoing embodiment, the rear foot bone complex may be in a settled full weight bearing condition.

In one possible embodiment of the method, the method includes placing a marker on the tibia of a test subject that enables tracking of the movement of the talus relative to the axis; providing a template for aligning the foot in a first or second position; and observing the displacement of the talus as indicated by the marker relative to the first or second position while allowing a displacement of the rear foot bone complex.

In the foregoing embodiment, the method may further include a step of providing a calibrated scale for observing the displacement of the talus. In the foregoing embodiment, the marker may include a transmitter and a receiver; a light emitter; and/or a laser diode. In the foregoing embodiment, calibrated laser sensors may be provided to detect a laser beam projected by the laser diode. In the foregoing embodiment, the template may include an alignment guide adapted to align the foot in a neutral position. The forgoing method may further include a step of providing force sensors to determine weight distribution in the area of the foot corresponding to the metatarsal bones while allowing displacement of the rear foot bone complex. In the foregoing embodiment, the force sensors may include a signaling device to indicate a neutral position of the foot; a pronation position of a foot; a supination position of a foot; and/or a signaling device to indicate weight bearing from at least one metatarsal bone.

In the foregoing embodiment method, the force sensors may include at least one load bearing sensor to detect weight distribution on the metatarsal bones, and an indicator for visual display of the weight distribution.

In another possible embodiment, the inventive subject matter includes a system for assessing pronation in the foot, including a marker attachable to the anatomy of a test subject and allowing for observation of the motion of the talus from a first position to a second position based on transmission of a signal; and force sensors to indicate weight distribution in the area of the foot corresponding to the metatarsal bones, while allowing a displacement of the rear foot bone complex. In the foregoing embodiment, the system may further include a processor for calculating the displacement caused by the motion of the talus and relating the displacement to an amount of pronation, and/or an output device for displaying the amount of pronation.

These and other embodiments are described in more detail in the following detailed descriptions and the figures.

The foregoing is not intended to be an exhaustive list of embodiments and features of the inventive subject matter. Persons skilled in the art are capable of appreciating other embodiments and features from the following detailed description in conjunction with the drawings.

BRIEF DESCRIPTION OF THE DRAWINGS

The following figures show various embodiments of inventive subject matter (except where prior art is noted).

DETAILED DESCRIPTION

Figure 1A:
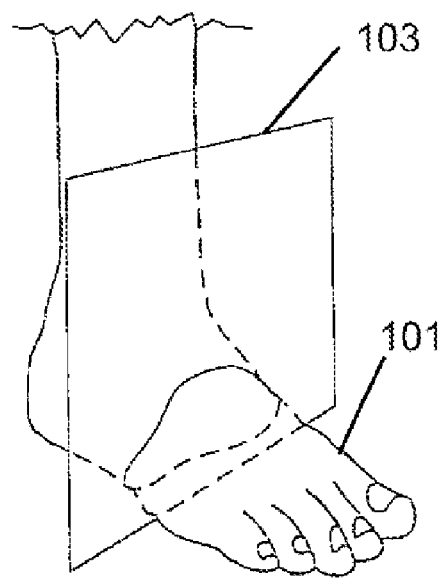
FIGS. 1A-C show a human foot and associated anatomical planes.

Representative embodiments according to the inventive subject matter are shown in FIGS. 1-14C, wherein similar features share common reference numerals.

In the figures, certain components, features or layers may be exaggerated for clarity.

Figures 1B, 1C:
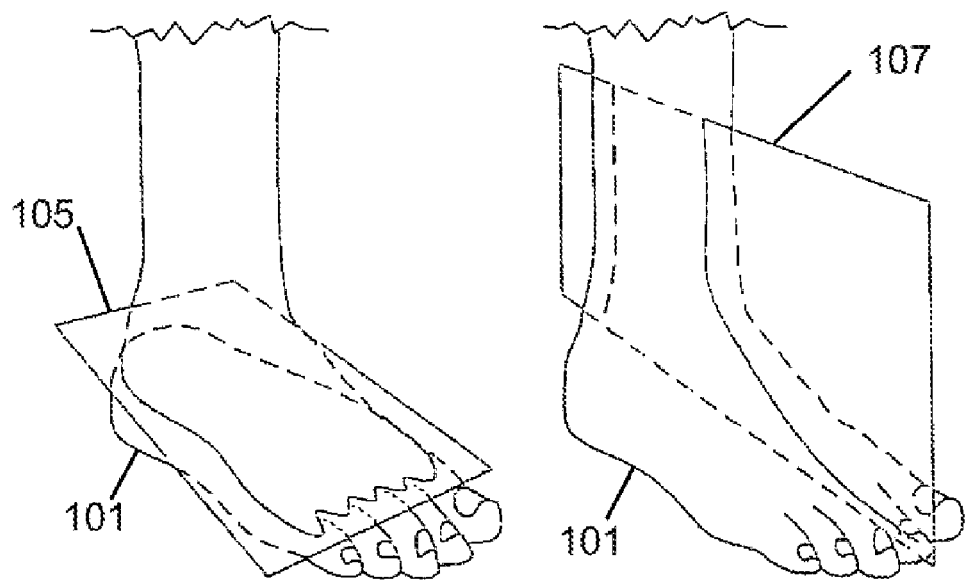
Figure 2:
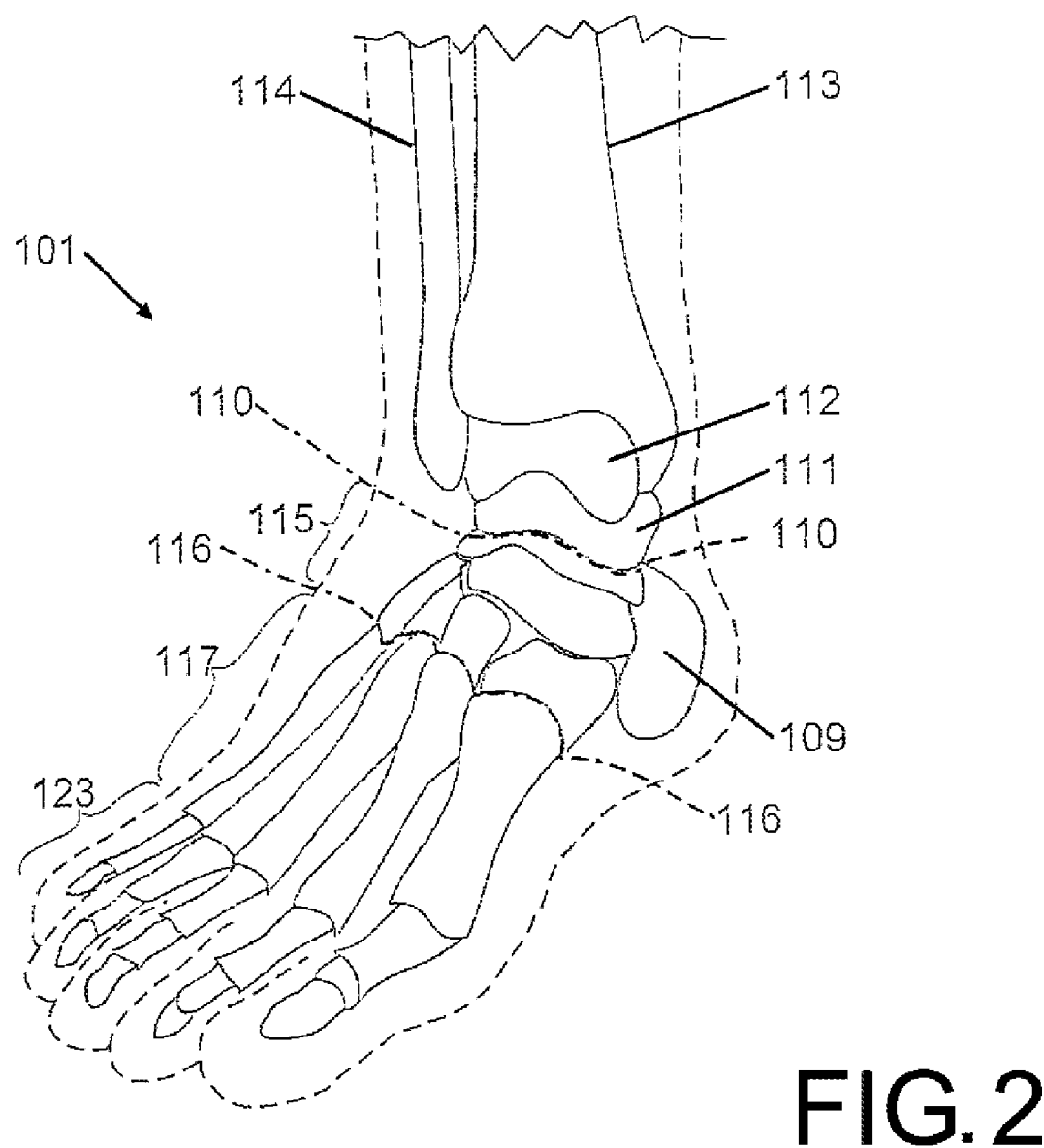
FIG. 2 shows the bones of the foot of FIG. 1.
Figure 3:
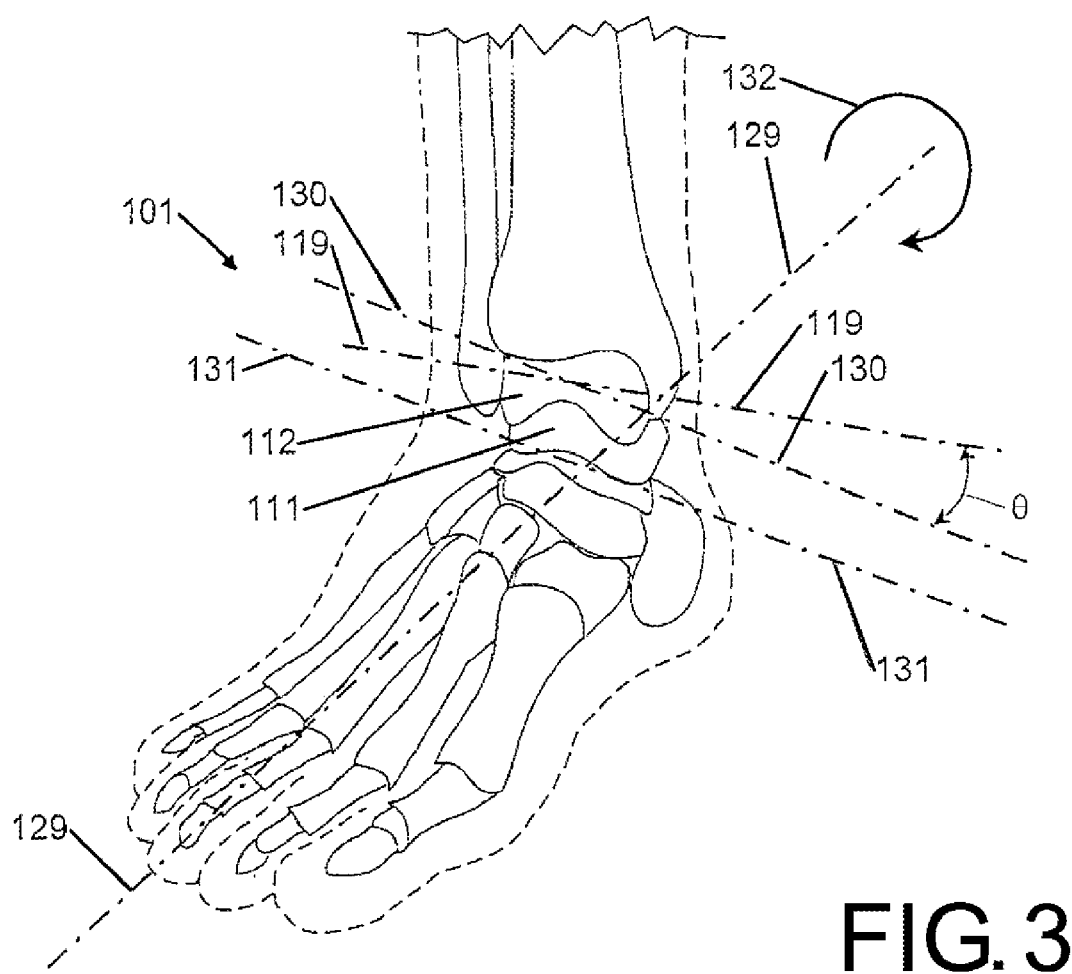
FIG. 3 shows several reference lines associated with the foot of FIG. 1.

FIGS. 1A, 1B, and 1C show three anatomical planes with respect to a human foot 101: the frontal plane 103, the transverse plane 105, and the sagittal plane 107. The frontal plane divides the foot front-to-back. The transverse plane runs through the heel and divides the foot top-to-bottom. The sagittal plane divides the foot left-to-right. FIG. 2 shows the bones of the foot of FIG. 1. The foot 101 includes seven tarsal bones 115, five metatarsal bones 117, the phalanges 123, the calcaneus 109, and the talus 111. Also referenced are the talar-head 112, tibia 113 and the fibula 114. FIG. 2 also shows various reference lines with respect to the foot 101 of FIG. 1 including lines representing the transmalleolar axis (TMA) 119, subtalar joint 110, and midtarsal joint 116.

This invention is based on the observation that an overpronated foot has an abnormally medially positioned talar-head 112. The talar-head is internally rotated in relation to the calcaneus 109. Thus, the more medially deviated the subtalar-joint axis 131 (shown in FIG. 3), the greater the magnitude of pronation. The amount of pronation can be observed when the foot rotates from a neutral position to a relaxed position. The subtalar-joint-neutral position is defined below. The pronation-based rotation is translated to movement of the talus 111 because both the subtalar-joint axis 131 and the midtarsal-joint-oblique-axis 129 pass through the talus 111.

The inventive subject matter disclosed herein exploits the discovery that pronation may be re-defined as medial deviation 130 of the subtalar-joint axis 131, rotation 132 about the midtarsal-joint-oblique-axis 129, and adduction and plantar flexion of the talus 111. This motion manifests itself as movement of the talar-head 112. Accordingly, the inventive subject matter disclosed herein includes a system that facilitates observation of motion of the talar-head 112 as the foot 101 displaces from the neutral position to the relaxed position.

Figure 4:
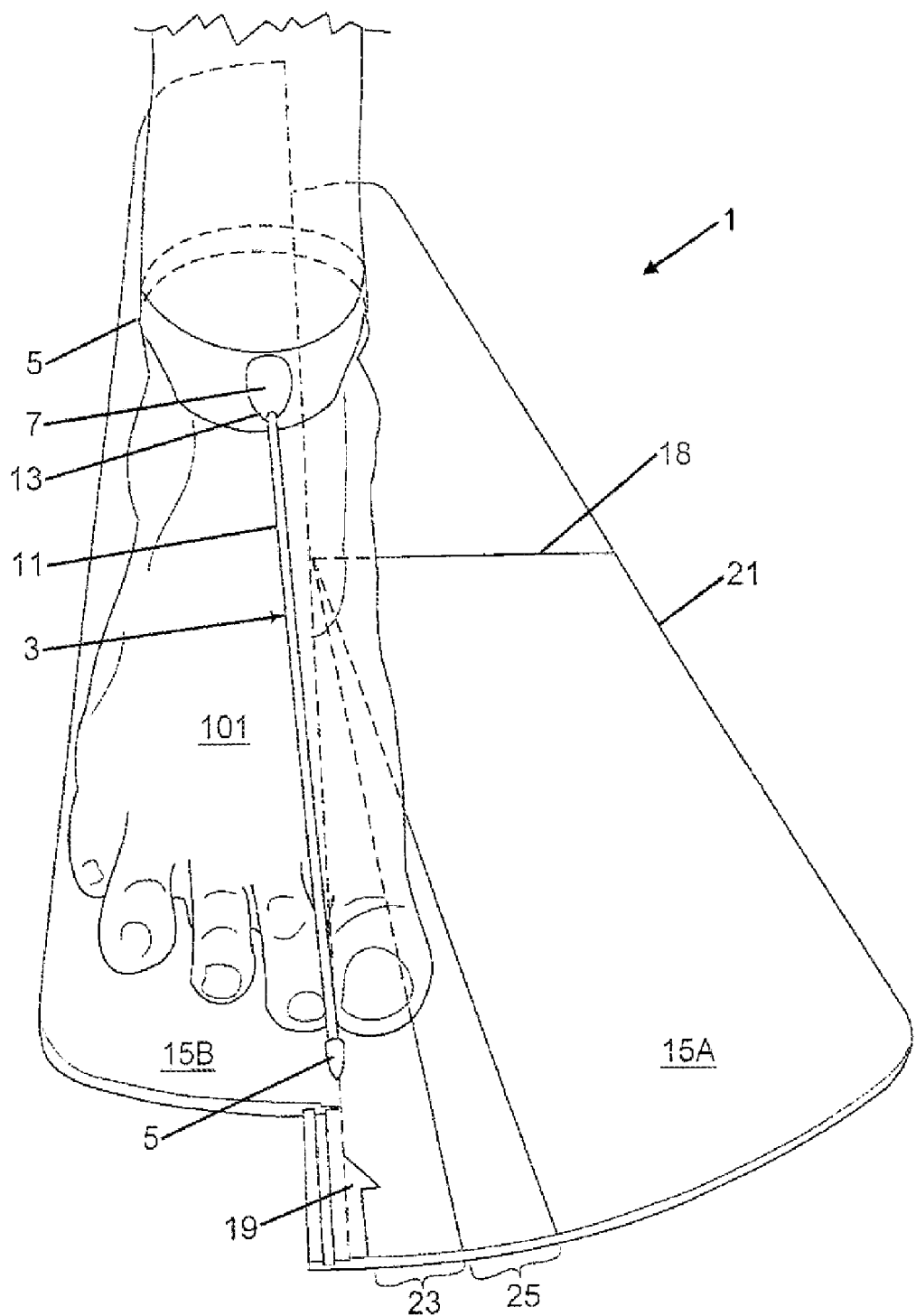
FIG. 4 is a schematic representation of the foot in a first position in relation to one embodiment of a foot assessment system.
Figure 5:
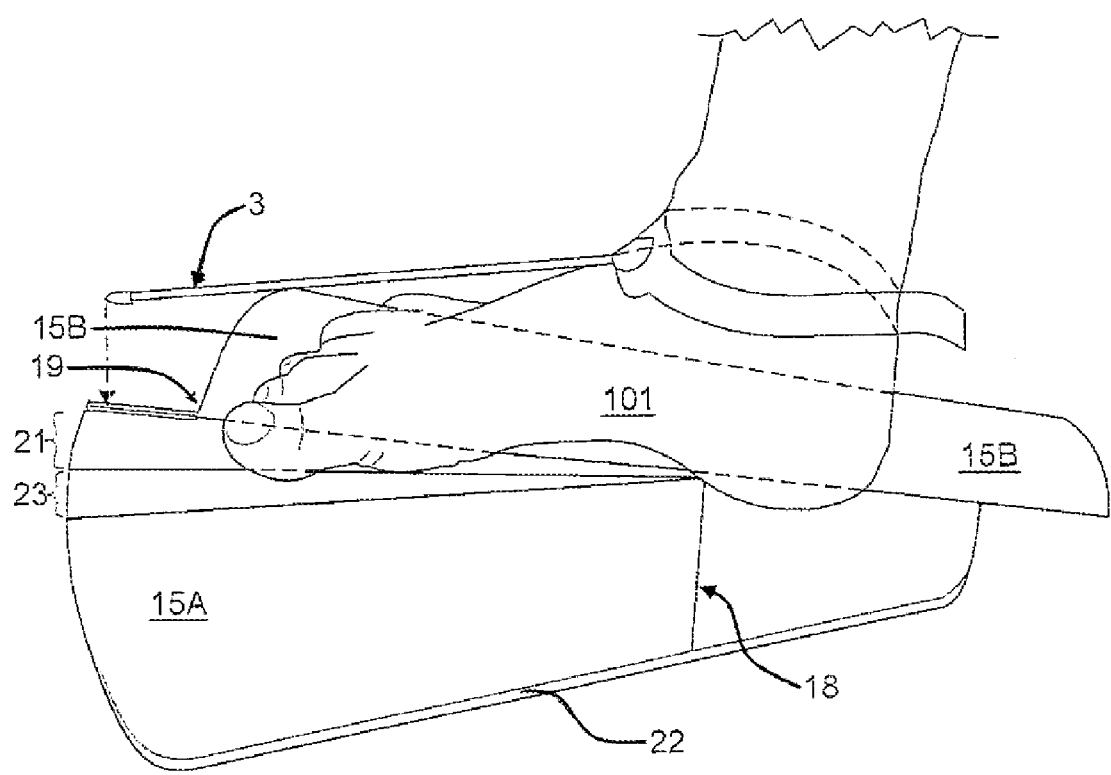
FIG. 5 is a profile of the image of FIG. 4.
Figure 6:
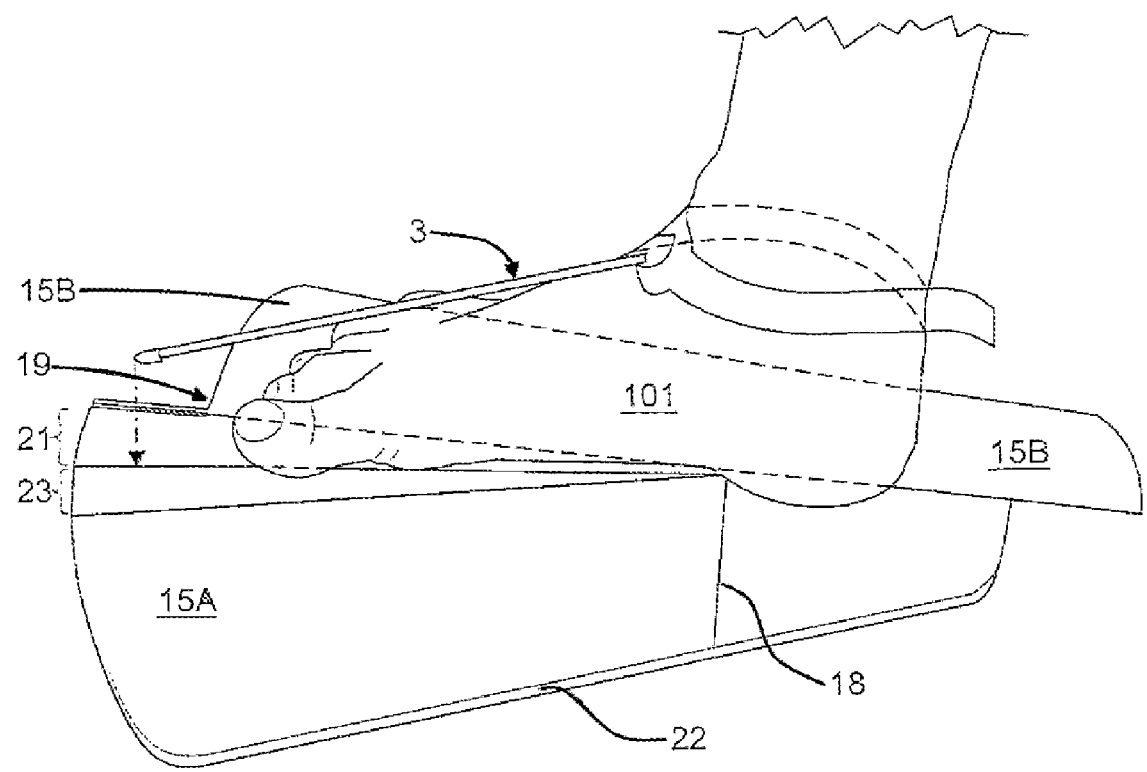
FIG. 6 is a schematic representation the foot of FIG. 4 in a second position.

FIGS. 4-6 show a possible embodiment of a foot assessment system according to certain inventive subject matter disclosed herein. The system includes a marker, for example, indicator 3. The elongated indicator 3 has a relatively long shaft 11 with a distally located tip 9. At an end opposite the tip 9, the base 13 of the shaft is coupled to a mounting surface 5 having means for attaching to the foot 101. The means for attaching to the foot may be straps, tape, or self-adhesive pad, for example. The shaft 11, firmly secured to the talar-head 112, amplifies rotation of the foot as it transitions from a first position to a second position.

The system may further include an optional template 21. The template adapts to align the foot in an initial or first position. For example, the template 21 includes an alignment guide, such as reference line 19. When the foot is in the subtalar-joint-neutral position (initial position) and the indicator 3 is properly adjusted and secured, the longitudinal axis of the shaft 11 will coincide with the reference line 19.

The template 21 may include two plates (15A and 15B), which are adjustable with respect to each other. Each plate 15A and 15B may include an ankle-joint reference line 18, which corresponds with the foot's transmalleolar axis 119 when the foot 101 is properly aligned in the neutral position. Typically, the TMA 119 is inclined about 20 to about 23 degrees in lateral rotation (indicated by "θ" in FIG. 3) to the frontal plane when viewed from a perspective normal to the transverse plane 105. Aligning the anklebone with ankle-joint reference line 18 also may align the foot 101 in the first, neutral position.

The template 21 also receives the foot in second, relaxed position. One enhancement to the template 21 may include a first pronation zone 23, indicating a normal range of pronation, and a second zone 25, indicating over-pronation.

In another embodiment, the system may include only a template 21. In another embodiment, the system may include only a marker. In fact, any combination of template, marker, both, or neither will assist observation of the talar head to varying degrees.

The foot assessment system may be made from a variety of materials such as paper, plastics, wood, lightweight metals, or various alloys. For example, a paper template might be mailed to a user for home-assessment. In another embodiment, the foot alignment template 21 or relevant lines or points thereon is drawn or marked on the floor or other object that the foot stands upon. The system may be provided to a point-of-sale location to facilitate the selection of footwear.

Figure 7:
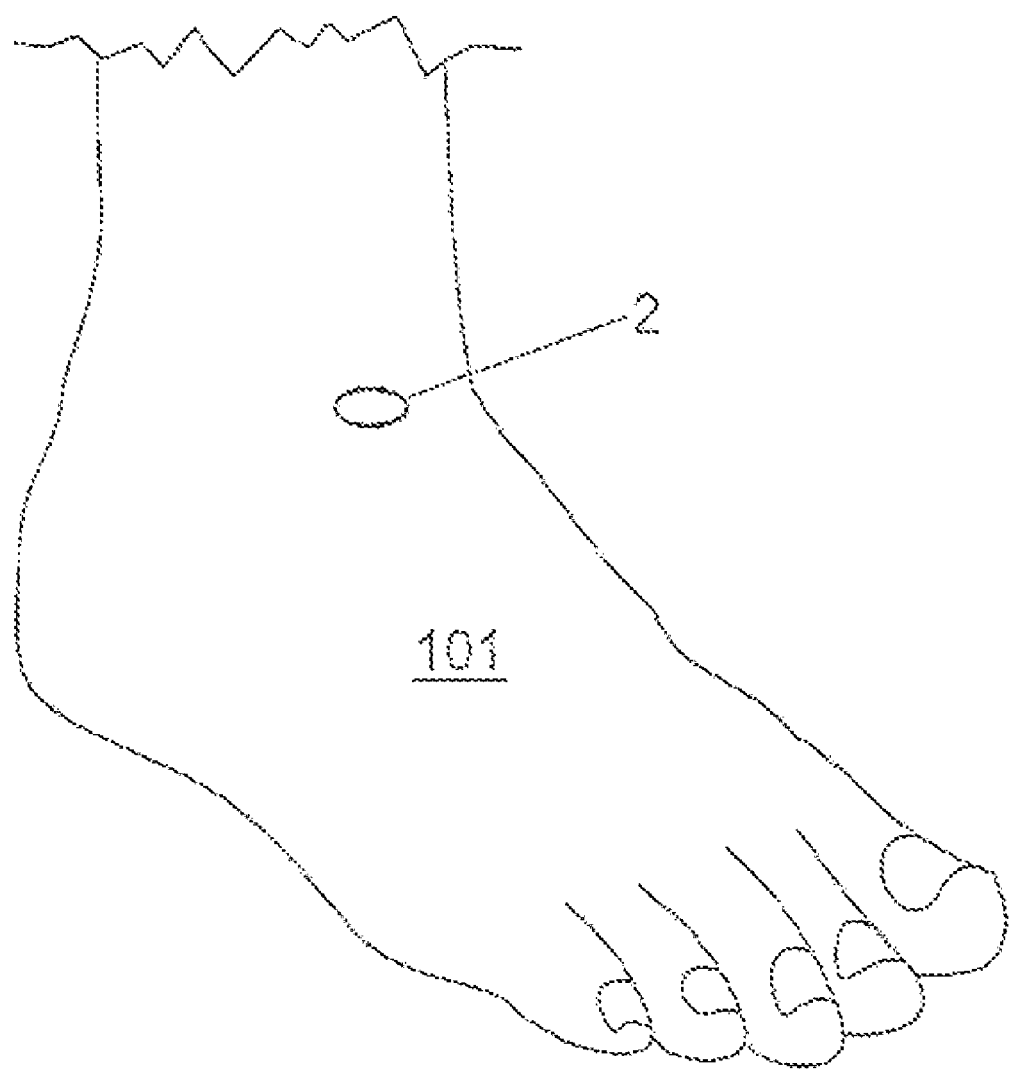
FIG. 7 shows another embodiment of a foot assessment system.
Figure 8:
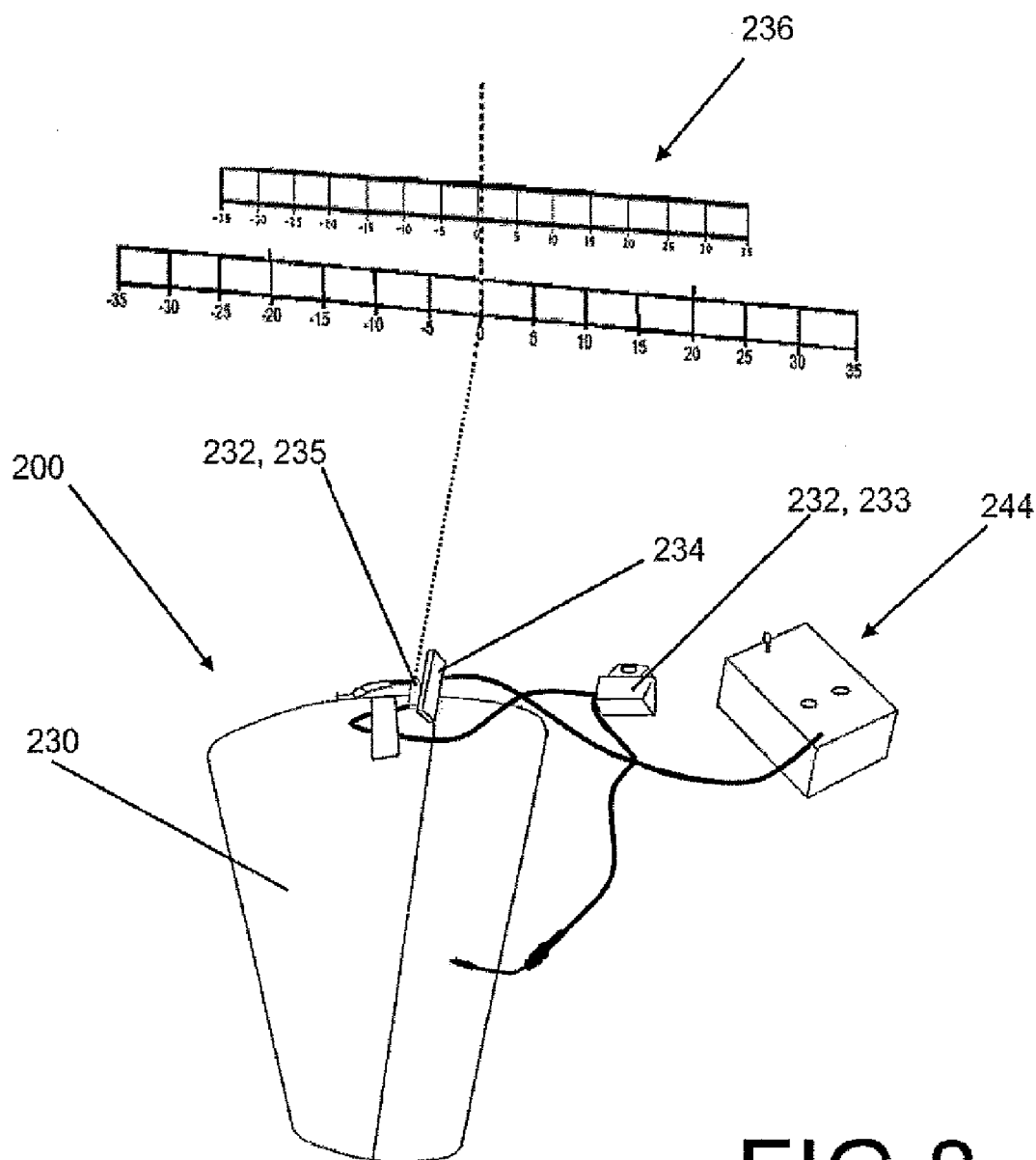
FIG. 8 shows another possible embodiment of a foot assessment system.

The marker may be anything that facilitates observation of movement of the talar-head region 112 of the foot as it moves from the first position to the second position. For example, as shown in FIG. 7, the marker 2 could be an ink spot.

In another possible embodiment, the system may comprise a marker 2 made from a reflective material. A light source, such as an IR or laser light, may be reflected off the marker 2. As the talar-head rotates from the subtalar-joint-neutral position to the relaxed position, a sensor detects the amount of displacement. A processor calculates the displacement and relates the displacement to an amount of pronation and sends this information to an output device. Optionally, the output device selects a recommended range of footwear or orthotic insert from a database, which may be internal to the device, or remote and connected via a data-network, such as the Internet, for example.

In another inventive embodiment, a method is used to determine the relative amount of pronation. The method may be used independent of any particular device and may be based solely on observation of relative movement of the foot. The method includes the steps of placing a subject foot 101 in the neutral position (shown in FIG. 5, for example). An observer observes the location of the foot 101 in this first position. Next, while watching the talar-head region 112, the foot rotates to a second, relaxed position (shown in FIG. 6, for example). The amount of rotation of the talus 111 at the talar-head 112 corresponds to the amount of pronation.

Optionally, the method according to the inventive subject matter disclosed herein may incorporate the system as described herein. A template 21 is placed under the foot 101. A marker 2 or an indicator 3 is attached to the foot over the region near the talar-head 112. Then, the foot 101 is placed in the subtalar-joint-neutral position. The indicator 3 is secured to the foot and adjusted so that the longitudinal axis of the indicator coincides with a reference line 19 when viewed from a normal perspective to the template 21. The observer observes an initial position 15 of the indicator 3. Next, the foot 101 rotates to the relaxed position. The observer observes the second position of the indicator 3 in relation to the template 21. The relative movement from the indicator's first position 15 to the second position 17 correlates to the amount of pronation. The template 21 may include aids to assess pronation including pronation zones: a first zone 23 indicates a range of normal-pronation, a second zone 25 indicates over-pronation. Thus, when the foot 101 is in the relaxed position and the indicator 3 is viewed generally normal to the template 21, the tip 9 overlaps one of the regions on the template 21.

Another embodiment of the inventive subject matter disclosed herein includes a method of selecting footwear. This method includes placing the foot 101 in a first position, moving the foot to a second position, observing the relative displacement of the talar-head 112; the displacement corresponding to an amount of pronation of the foot, and selecting footwear based on the amount of pronation. For example, an over-pronating foot may benefit from a stability or motion-control running shoe.

Another possible inventive embodiment may include a database, which may contain a classification of shoes, orthotic inserts, or both. The database may be organized in any logical manner, such as, brand, activity type (running, walking, hiking, cross-training, standing, or suitable for individual recovering from medical procedures, for example), model, pronation-correcting type, or other useful categories, for example. The database may be accessed via the Internet or an intranet, it may reside on a personal computer, or it may be a look-up table that is conveniently located at a point-of-sale, for example.

Another possible embodiment of the inventive subject matter disclosed herein is illustrated by FIGS. 8 and 9A-E, which show a foot assessment system adapted to assess displacement of the talus relative to an axis of the foot by marking the anatomy of a test subject to enable tracking of the movement of the talus relative to the axis, and aligning the foot in a first position, and observing the displacement of the talus as indicated by the marking relative to the first position while allowing displacement of the rear foot bone complex. In particular, this system allows for assessment of normal and abnormal pronation by measuring the rotation of the talus from a first, neutral position to a second, relaxed position while allowing displacement of the rear foot bone complex. The rear foot bone complex is defined as a bone complex formed by the calcaneous and the talus. The talus bone supports the tibia and fibula at the ankle joint. The talus bone further rests on the calcaneous bone, with the subtalar joint extending between these two bones. The weight of the individual is transferred from tibia and fibula to talus bone and subsequently to calcaneous bone. The neutral position is the position of the subtalar-joint in which the foot is neither supinated nor pronated. In this position, the concave surface of the calcaneous and convex surface of the talus are congruous.

It is particularly advantageous to allow a displacement of the foot while the foot is under a predetermined load. The predetermined load on the foot is full weight bearing. A foot is full weight bearing when a subject's entire body weight is distributed equally over both legs and feet, and resulting in the rear foot bone complex being in a settled full weight bearing condition, that is, when a person is standing, the full body weight is distributed over both feet.

The components of the system shown in FIGS. 8 and 9A-E are described below.

The system allows measuring of maximum pronation and maximum supination of the foot. The displacement of the talus under these circumstances is a direct indicator of the amount of abnormal pronation. A basic requirement to the functions of the lower extremities, in all forms of activity, is the ability of gaining stability in order to demonstrate mobility. Pronation is a reaction caused by the effects of gravity and ground reaction forces. Supination is a reaction as a result of pronation. Pronation and supination occur at all joints and in all planes of motion within the locomotion systems from the foot to the low back.

Pronation is dominated by eccentric (deceleration) muscles function. Supination is dominated by concentric (acceleration) muscle function. The transformation of pronation into supination is dominated by isometric (stabilizing) and the deceleration of motion at one joint and the acceleration of motion at another joint, all at the same time. These motions depend upon the effects of gravity. Given the above criteria the motions of pronation and supination can only be assessed in a full weight bearing stance position. These motions occur as noted in all three cardinal body planes: transverse, frontal and sagittal; and all at the same time, to greater and lesser degrees, depending upon the specific joint. Because the subtalar joint axis and midtarsal joint oblique axis both pass through the body of the talus, a triplane motion, i.e., in all three planes and both joints, can be accurately assessed by observing the motions of the talus. The motions of pronation and supination occur in all joints of the lower extremity: foot, ankle, knee, hip and pelvis, and in all three planes. Therefore, a non-weight bearing or semi-weight bearing seated position of the foot and lower extremity cannot produce true pronation and supination When "raising" and "lowering" the arch in a semi weight bearing, seated position, the primary plane of motion would occur in the frontal plane, with little or no motion occurring in either the sagittal or transverse planes, especially rotation in the transverse plane.

The pelvis, foot and lower extremity can only pronate and supinate in an orchestrated and coordinated manner when the kinetic chain is fully loaded, i.e., fully weight bearing "closed kinetic chain." The motion of the talus as a result of gravity initiates this entire kinetic sequence of coordinated motions.

Figure 10:
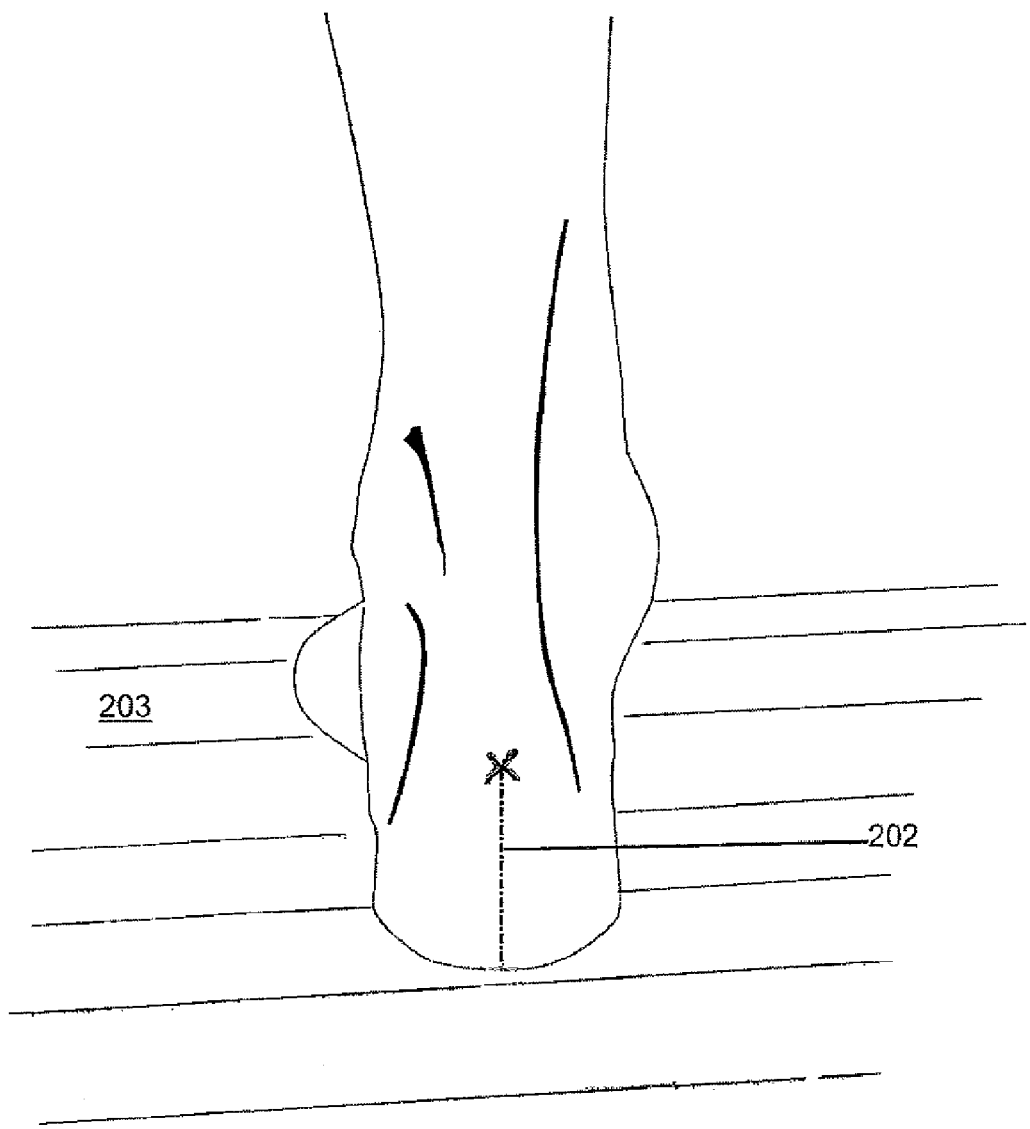
FIG. 10 shows a detail of a right foot in a neutral position.
Figure 11:
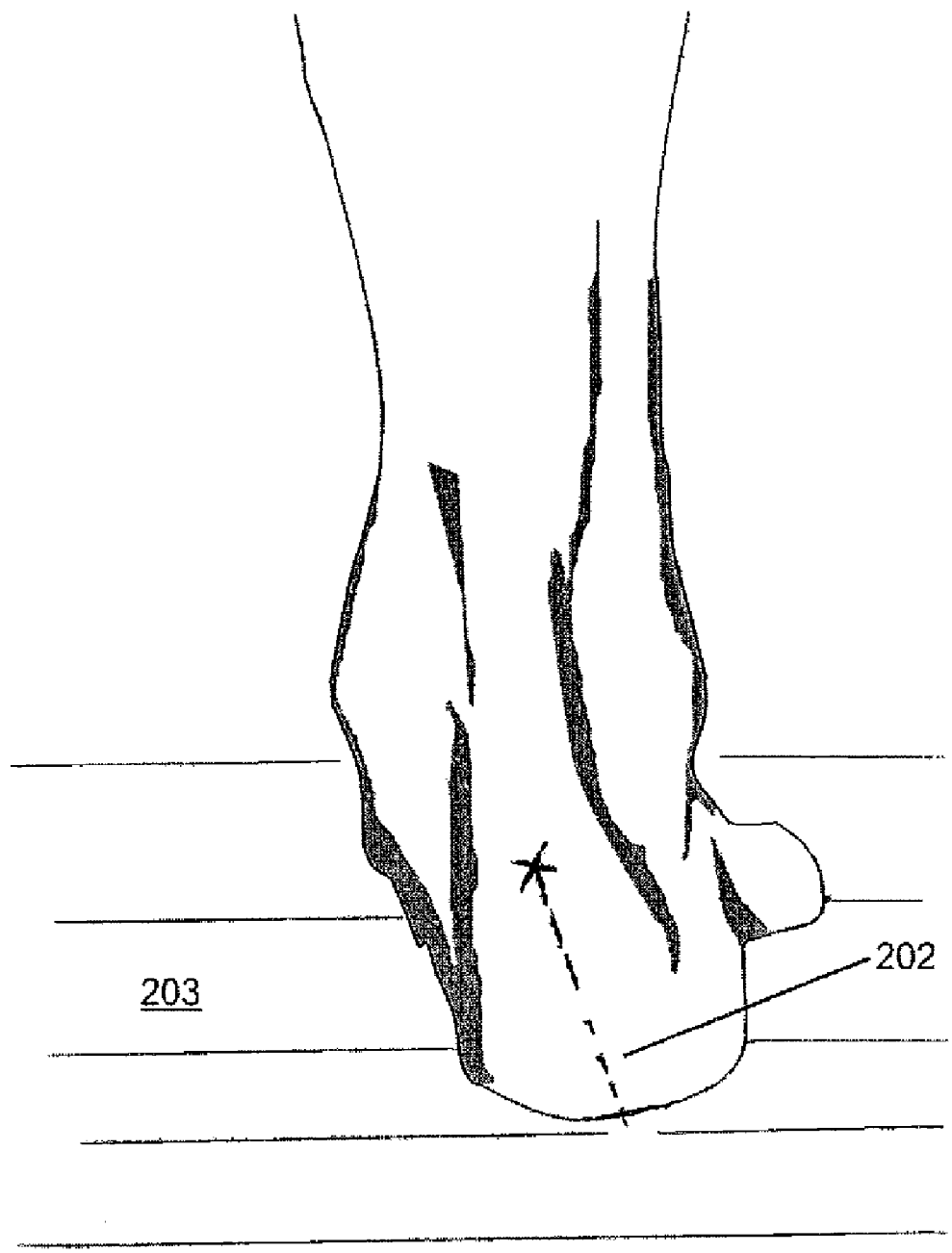
FIG. 11 shows a detail of a right foot in a pronated position.
Figure 12:
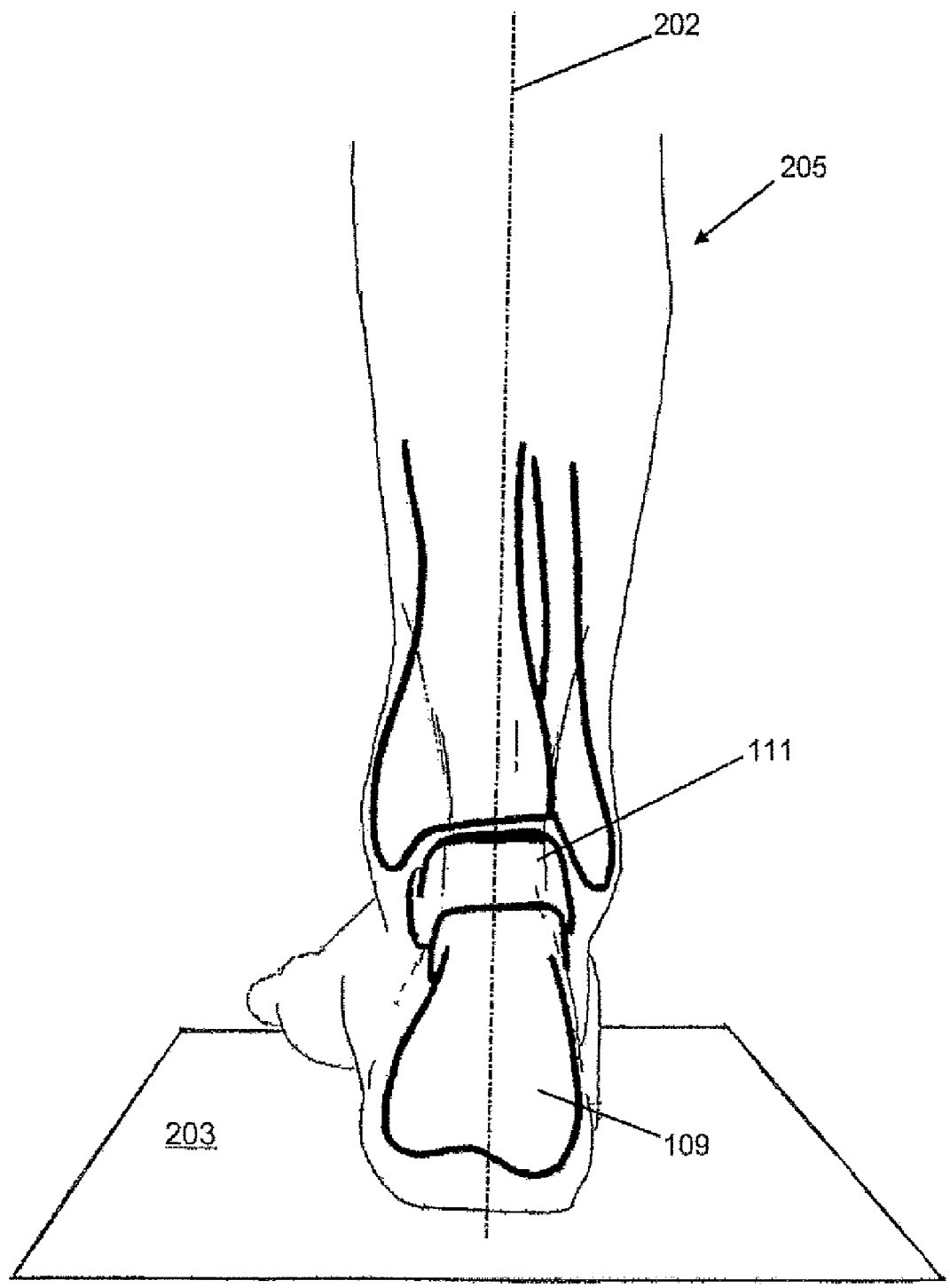
FIG. 12 shows a closed chain neutral of the subtalar joint
Figure 13:
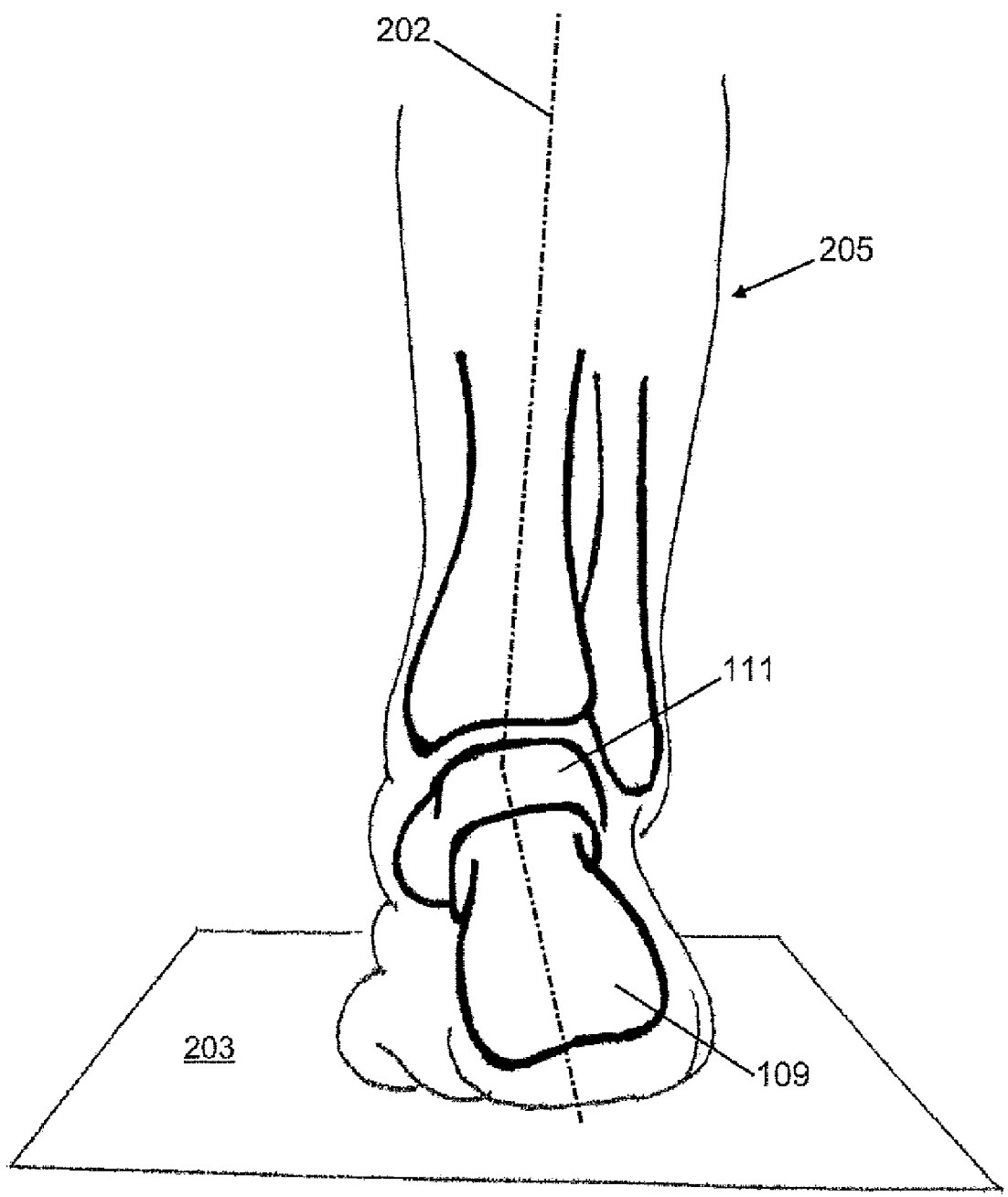
FIG. 13 shows a closed chain pronation of the subtalar joint.

FIGS. 10-13 illustrate a closed chain of the subtalar joint in the neutral and pronation positions of a right foot with a central axis 202 on a floor 203, FIGS. 10 and 12 illustrate the neutral position whereby the knee extends, the leg 205 rotates externally, the talus 111 abducts and dorsiflexes, and the calcaneus 109 inverts. FIGS. 11 and 13 illustrate the pronation position, whereby the knee flexes, the leg 205 rotates internally, the talus 111 abducts and plantar flexes, and the calcaneus 109 everts.

Figure 14A:
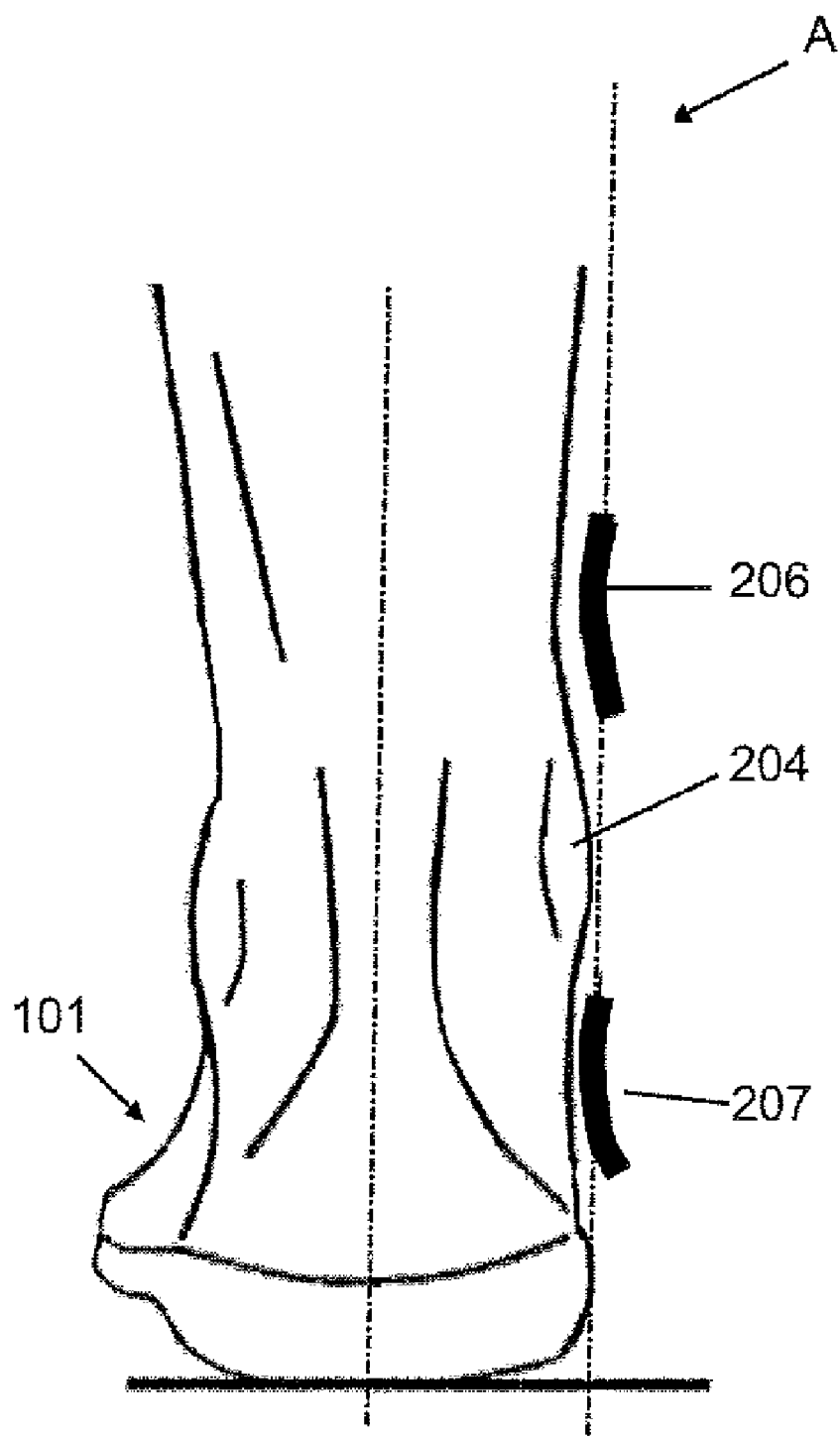
FIG. 14A-C shows a right foot with lines indicating the curves of the lateral malleolus angles in neutral, pronated, and supinated positions respectively.
Figure 14B:
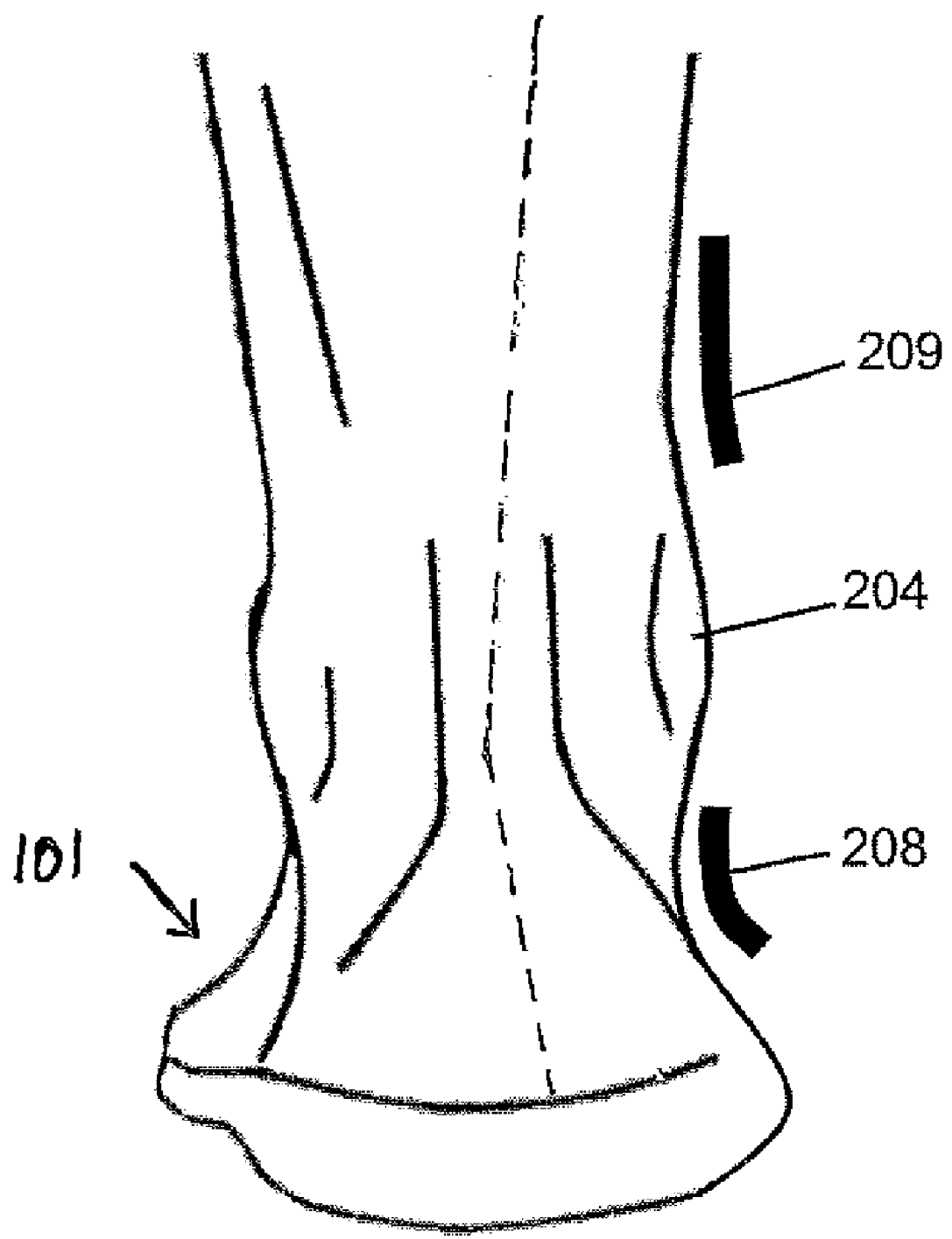
Figure 14C:
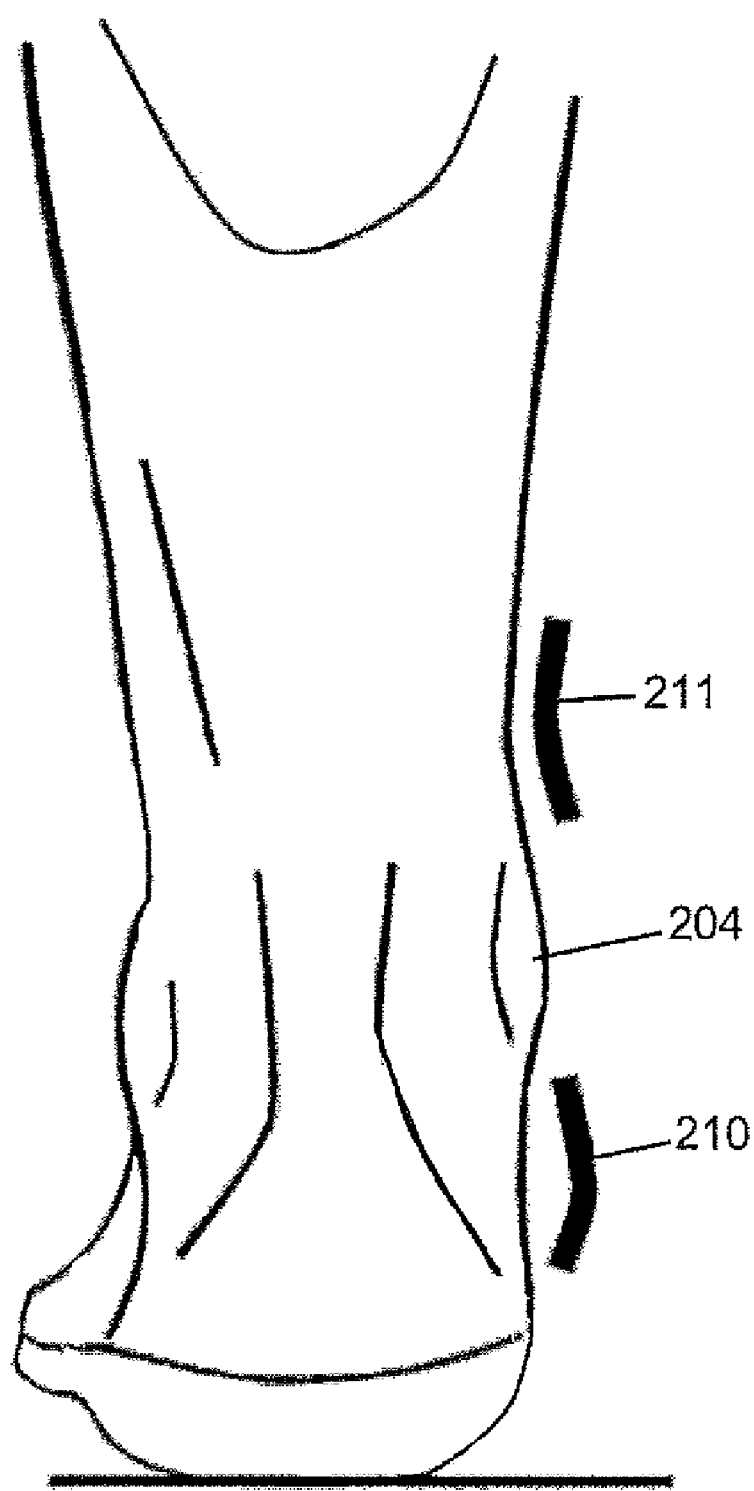

FIGS. 14A-C show a right foot, with lines indicating the curves of the lateral malleolus angles in neutral, pronated, and supinated positions respectively. FIG. 14A shows a foot 101 in a position that is neutral, i.e, neither pronated nor supinated at the subtalar joint. In this position, the directions of the curves 206 and 207 above and below the lateral malleolus 204 are relatively parallel with each other. This relationship is clinically useful in determining when the foot is in its neutral position.

The neutral position may be achieved by distributing the weight evenly over the feet. A foot may be in either a pronation or supination position, and rotate subsequently to a neutral position. The neutral position is reached when a straight line is formed along the leg, on the side of the foot and the ankle bone. As can be seen in FIG. 14A, a straight line A may be formed tangent to the curves 206 and 207, and perpendicular to the floor. For example, a bar may be used to help determine the neutral position. The bar may be positioned along the calf of the leg at the outside of the ankle bone, aligning curves 206 and 207 above and below the lateral malleolus 204.

FIG. 14B shows a foot 101 in a pronated position. In this position, the curve 208 below the lateral malleolus 204 angles in an everted direction from the direction of the curve 209 above the lateral malleolus. Similarly, FIG. 14C shows a foot in a supinated position. The curve 210 below the lateral malleolus 204 angles in an inverted direction from the direction of the curve 211 above the lateral malleolus. The lower curve 210 becomes less concave and then develops a convexity as the subtalar joint becomes progressively more supinated.

FIGS. 8, 9A-E illustrate a system 200 for assessment of foot displacement, by placing a marker on the tibia of a test subject that enables tracking of the movement of the talus relative to the axis, and providing a template 230 for aligning the foot in a first or second position, and observing the displacement of the talus as indicated by the marker relative to the first or second position while allowing a displacement of the rear foot bone complex. The template 230 may include an alignment guide 234 adapted to align the foot in a neutral position. The system 200 may include a calibrated scale 236 for observing the displacement of the talus.

Figure 9A:
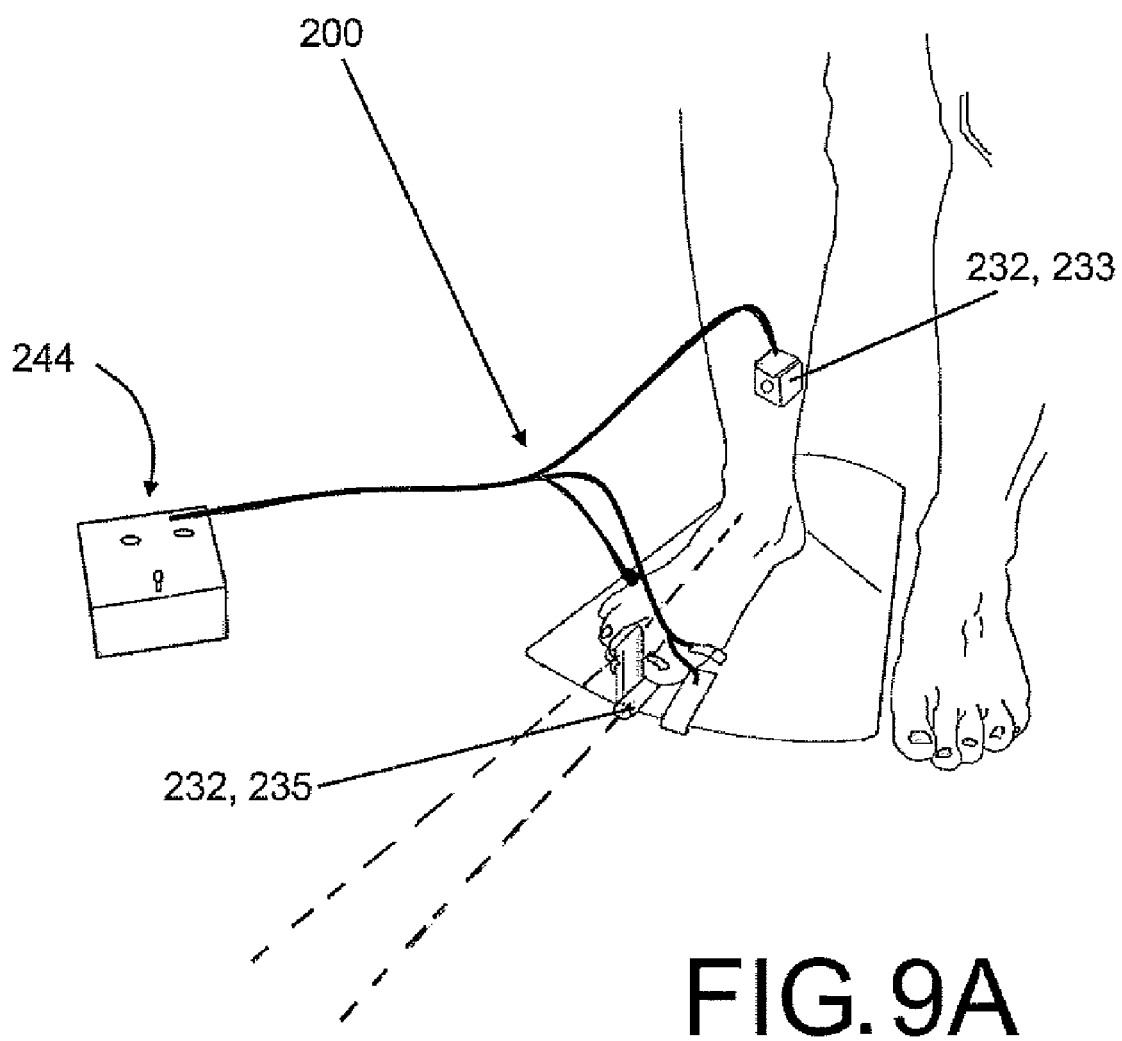
FIGS. 9A-E show several views of the embodiment shown in FIG. 8 when used on a right foot in a neutral position.
Figure 9B:
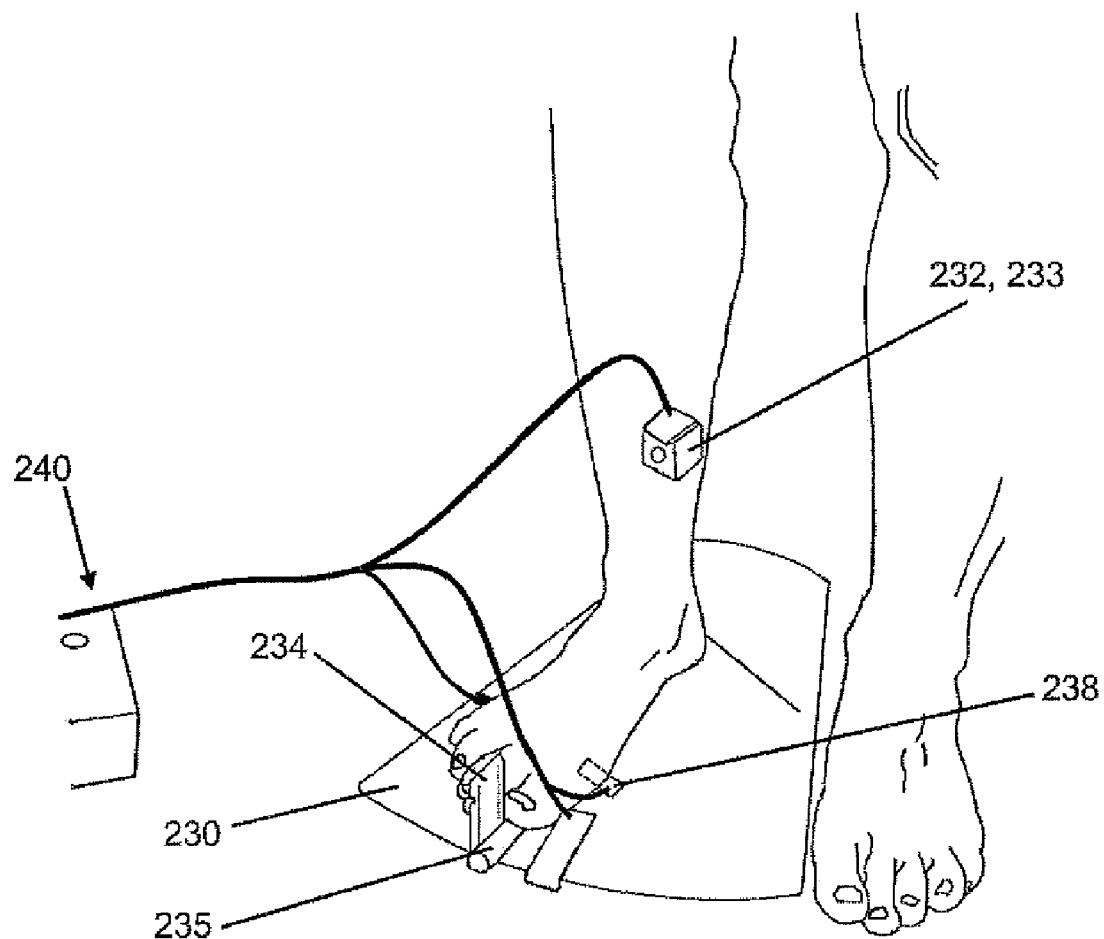
Figure 9C:
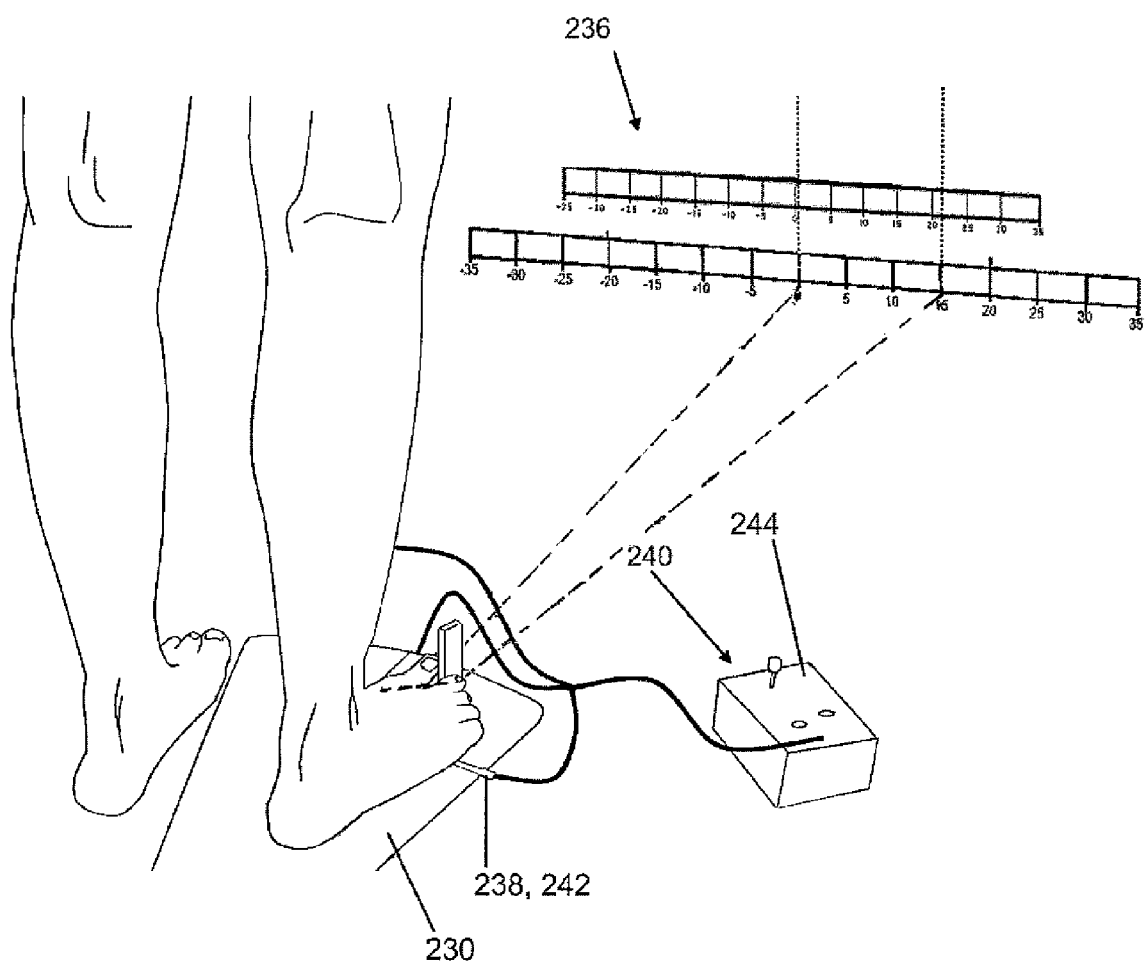
Figure 9D:
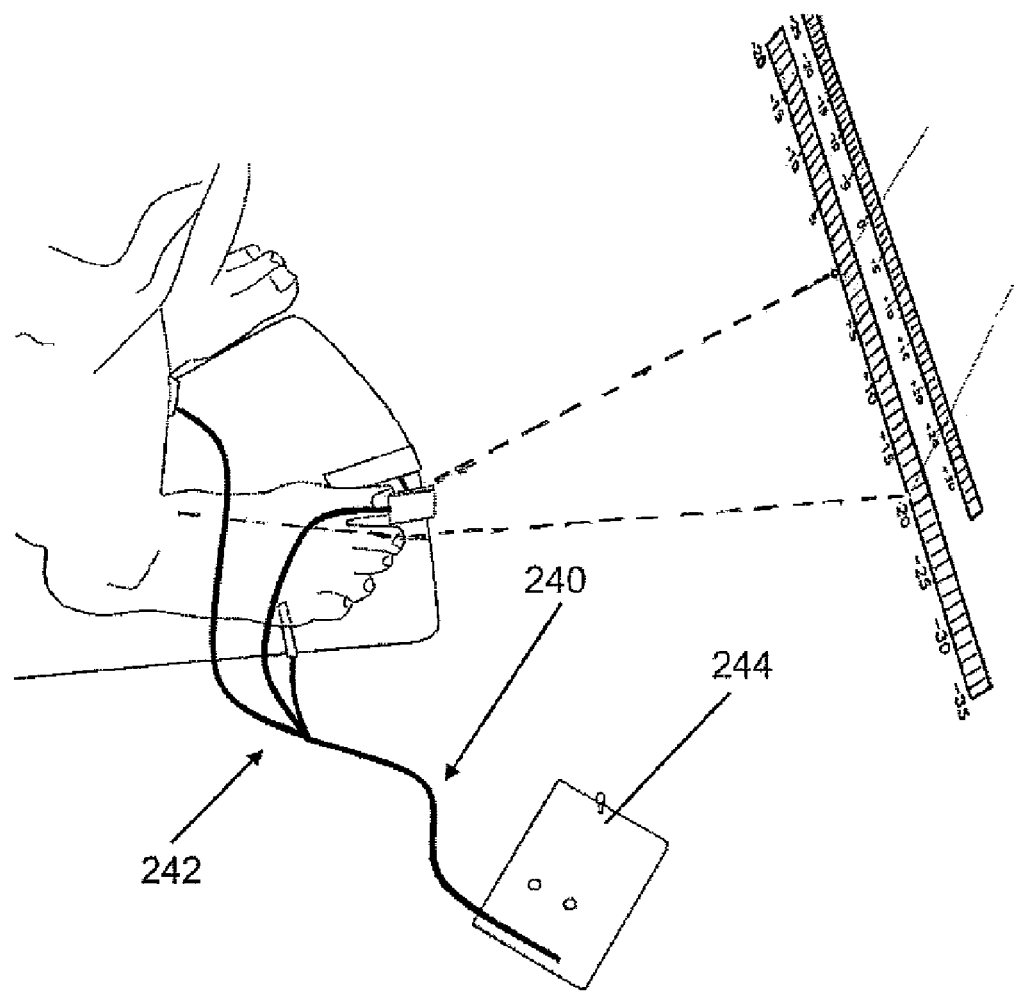

Similar to the template described before, the template 230 may be adapted to align the foot. As illustrated by FIG. 9B, the template 230 includes an alignment guide 234 for longitudinal alignment of the foot and a user LED 235 that provides for alignment with the zero point on the measuring grid. As described above, the template 230 may optionally include two plates, which are adjustable with respect to each other. The foot assessment system may include only a template or only a marker, or both to assist observation of the motion of the talus.

The foot assessment system may have a marker, for example transmitter 232 in FIGS. 8 and 9A-E, attachable to the anatomy of a test subject, and allowing for observation of the motion of the talus from a first position to a second position based on transmission of beams. The transmitter transmits a detectable signal to a receiver. The combination of emitter and receiver facilitates a determination of a displacement of the portion of the anatomy onto which the transmitter is disposed. The receiver may be any device or object that can receive the signal, for example, an electronic sensor, photosensor, or a display device that allows a human to visually perceive the signal, as is the case for the device shown in the figures.

The transmitter 232 may be defined as any means capable of producing a directed beam that allows following of the rotation of the foot as it transitions from a first position to a second. Suitable transmitter 232 may be, for example, a light source, such as an IR or laser diode, or radio waves. FIG. 8 and FIGS. 9A-E show a laser diode 233 mounted on the tibia, just above the ankle. In this particular area of the leg, the tibia is not covered with soft tissue, which can move, and thus allows the laser diode to respond directly to any movement of the tibia. Because tibia and talus rotate as a unit, accurate measurement of displacement of the talus is possible. The transmitter 232 may be firmly secured to the tibia by straps, tape, or self-adhesive pad, for example.

The system may include calibrated laser sensors to detect a laser beam projected by the laser diode. Displacement of beams may also be read by a beam sensitive scale or a beam sensor device, which relates to a processor to calculate the displacement. A processor may relate the displacement to an amount of pronation and sends this information to an output device. Optionally, the processor determines a recommended range of footwear or orthotic insert from a database, which may be internal to the system, or remote and connected via a data-network, such as the Internet, for example.

Figure 9E:
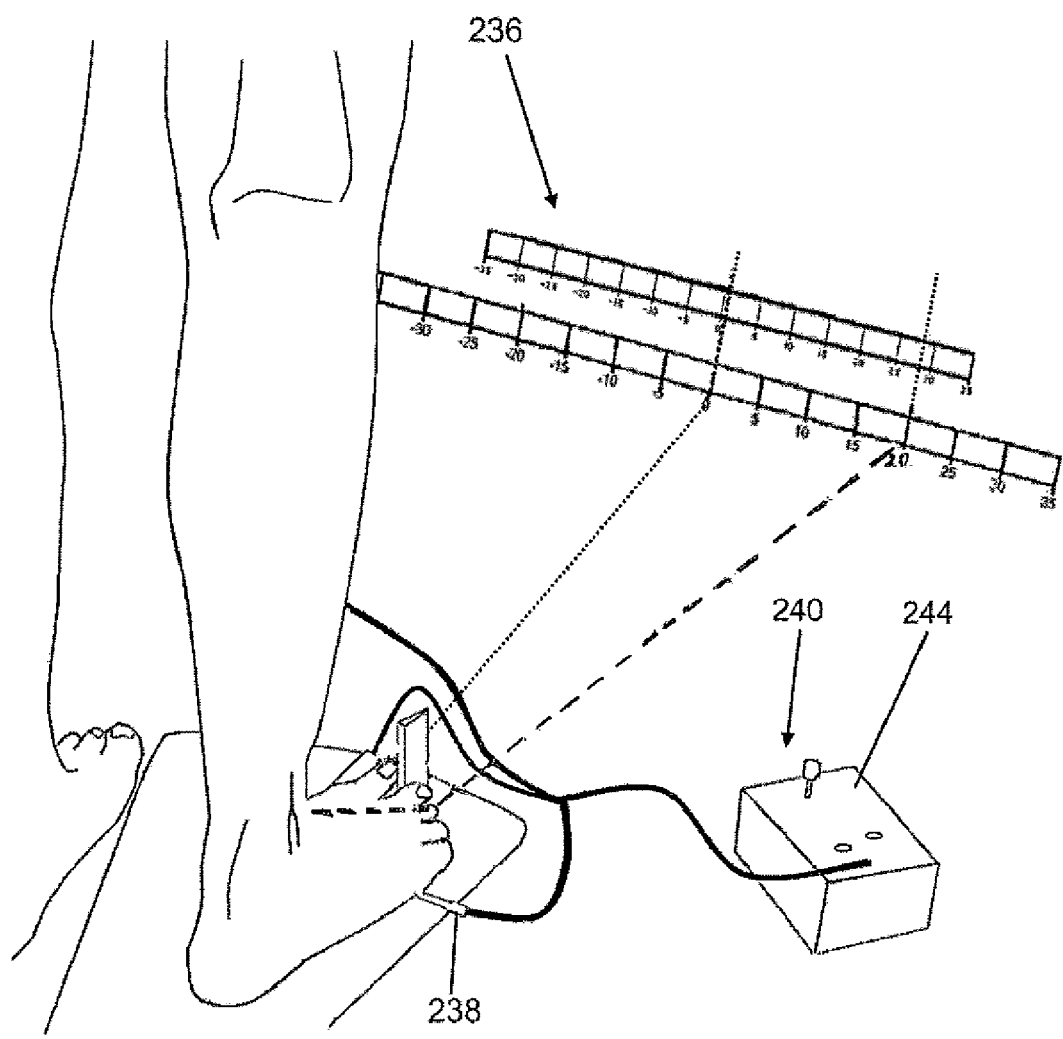

As the talar-head rotates from the first position to the second position, the displacement of the beams may be shown on a measuring grid or calibrated scale. The transmitter 232 may project a beam on a calibrated scale 236, such as shown in FIG. 9E, where the laser light emits a vertical beam on calibrated scale 236. The calibrated scale may be either numbered or include a light sensitive material or sensor for detecting the beam. For example, calibrated laser sensors could be used to detect a laser beam projected by the laser diode.

The system may further include one or more force sensors for sensing the weight at predetermined areas under a user's foot. Thereby the system can evaluate changes in force in relation to certain movements of the anatomy. These force sensors provide data about weight distribution in the foot. These data may be used in a system that includes an output device, which may for example give an indicating of certain threshold changes. For example, as shown in FIGS. 8 and 9A-E, the foot assessment system 200 may include force sensors 238 to sense a predetermined weight distribution in the area across the metatarsal bones of a foot. The weight distribution is measured while allowing displacement of the rear foot bone complex under the weight of a user as shown in FIGS. 10-14, for instance. The force sensors may include a signaling device to indicate a neutral position of the foot, a pronation position of a foot, or a supination position of a foot.

As illustrated in FIGS. 9B-E, force sensors 238 may be connected to an output device 240 to indicate weight bearing from at least one metatarsal bone. For example, load bearing sensors 242 may detect weight on the first and fifth metatarsal bones and relay the information to a visual display, such as a green/red LED 244.

In another possible embodiment, the inventive subject matter is directed to a method for assessing displacement of the talus relative to an axis of the foot, which may incorporate a foot assessment system as described above. According to this method, the talus is first observed in a neutral position. Then the amount of pronation is assessed by observing the displacement of the talus from a first, neutral position to a second, relaxed position, and the observation is facilitated by placing a transmitter on a test subject's anatomy. Force sensors may indicate weight distribution in the area of the foot corresponding to the metatarsal bones, while allowing a displacement of the rear foot bone complex.

FIGS. 8 and 9A-E illustrate how a template 230, including sensors, may be placed under the foot 101. A marker or transmitter 232 is attached to the tibia. Then, the foot 101 is placed in the neutral position. A transmitter 232 is secured to the tibia and the foot is positioned in the neutral position and the position of the beam is noted on a measuring grid. Force sensors 238 indicate when a foot is in a full-weight bearing position. The force sensors may determine weight distribution in the area of the foot corresponding to the metatarsal bones while allowing displacement of the rear foot bone complex while the foot is full weight bearing. The observer observes an initial position of the beam. Next, the user shifts balance of the rear foot bone complex by rotating to the relaxed position. The observer observes the second position of the beam in relation to the calibrated scale 236. The relative movement from the indicator's first position to the second position correlates to the amount of pronation. The template 230 may include aids to assess pronation such as pronation zones, for example a first zone indicates a range of normal-pronation, a second zone indicates over-pronation.

A full range of motion may be indicated by the force sensors, for example, when using force sensors under the first and fifth metatarsals, keeping the foot under full weight and in contact with the ground, and subsequently allow the foot to rotate inwardly until there is no force on the fifth metatarsal. The rear foot bone complex is allowed to displace naturally during this process, yielding an accurate assessment of pronation.

Persons skilled in the art will recognize that many modifications and variations are possible in the details, materials, and arrangements of the parts and actions which have been described and illustrated in order to explain the nature of this inventive subject matter and that such modifications and variations do not depart from the spirit and scope of the teachings and claims contained therein.

All patent and non-patent literature cited herein is hereby incorporated by references in its entirety for all purposes.

The invention claimed is:

1. A method for assessing displacement of a talus relative to a predetermined axis of a foot and lower leg, comprising:
    marking an area of a test subject's lower extremities with a marker that assessably follows the movement of the talus to enable tracking of the movement of the talus relative to the axis;
    providing a template for aligning the foot;
    aligning the foot in a first position;
    moving the foot from the first position to a second position while allowing a displacement of a rear foot bone complex, and indicating the movement from the first position to the second position on the template so that a displacement of the talus is observed as indicated by the marking relative to the first position; and
    assessing displacement of the talus relative to the first position.

2. The method of claim 1, wherein the rear foot bone complex is in a settled full weight bearing condition in the first position.

3. The method of claim 1, wherein the marked area of a test subject's lower extremities is a tibia.

4. The method of claim 3, further comprising a step of providing and using a calibrated scale for observing the displacement of the talus.

5. The method of claim 3, wherein the marker includes a transmitter and a receiver.

6. The method of claim 3, wherein the marker includes a light emitter.

7. The method of claim 3, wherein the marker includes a laser diode.

8. The method of claim 7, further comprising providing and using calibrated laser sensors to detect a laser beam projected by the laser diode.

9. The method of claim 3, wherein the template comprises an alignment guide adapted to align the foot in a neutral position.

10. The method of claim 3, further comprising a step of providing and using force sensors to determine weight distribution in an area of the foot corresponding to a plurality of metatarsal bones while allowing displacement of the rear foot bone complex.

11. The method of claim 10, wherein the force sensors include a signaling device to indicate a neutral position of the foot.

12. The method of claim 10, wherein the force sensors include a signaling device to indicate a pronation position of a foot.

13. The method of claim 10, wherein the force sensors include a signaling device to indicate a supination position of a foot.

14. The method of claim 10, wherein the force sensors include a signaling device to indicate weight bearing from at least one metatarsal bone.

15. The method of claim 10, wherein the force sensors include at least one load bearing sensor to detect weight distribution on the metatarsal bones, and an indicator for visual display of the weight distribution.

16. A system for assessing pronation in the foot, the system comprising:
  a marker attachable to an area of a test subject's lower extremities that assessably follows the movement of the talus and allows for observation of a motion of the talus from a first position to a second position based on transmission of a signal;
  a template for aligning the foot in a first position and moving the foot from the first position to a second position while allowing a displacement of a rear foot bone complex, and wherein the movement from the first position to the second position is marked on the template so that a displacement of the talus is observed as indicated by the marking relative to the first position;
  force sensors to indicate weight distribution in an area of a foot corresponding to a plurality of metatarsal bones, while allowing a displacement of a rear foot bone complex so that the force sensors indicate a full range of motion of the metatarsal bones to assist in the assessment of pronation in the foot; and
  a processor programmed to calculate the displacement caused by the motion of the talus and relating the displacement to an amount of pronation to assess pronation in the foot.

17. The system of claim 16, further comprising an output device for displaying the amount of pronation.

\* \* \* \* \*